United States Patent
Baker et al.

(10) Patent No.: US 9,000,914 B2
(45) Date of Patent: Apr. 7, 2015

(54) PERSONAL AREA NETWORK PAIRING

(75) Inventors: Steven D. Baker, Beaverton, OR (US); Robert J. Kahlke, Milwaukie, WI (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1137 days.

(21) Appl. No.: 12/723,726

(22) Filed: Mar. 15, 2010

(65) Prior Publication Data

US 2011/0221590 A1 Sep. 15, 2011

(51) Int. Cl.
- *G08B 1/08* (2006.01)
- *A61B 5/00* (2006.01)
- *H04W 12/06* (2009.01)

(52) U.S. Cl.
CPC ............... *A61B 5/0002* (2013.01); *A61B 5/411* (2013.01); *H04W 12/06* (2013.01); *A61B 5/0024* (2013.01); *A61B 5/0028* (2013.01)

(58) Field of Classification Search
CPC .... A61B 5/0002; A61B 5/411; A61B 5/0024; A61B 5/0028; A61B 5/02158; H04W 12/06; G06Q 50/22
USPC ............ 340/539.12, 5.22; 455/41.2; 380/270; 600/301, 485; 705/2
See application file for complete search history.

(56) References Cited

U.S. PATENT DOCUMENTS

| | | | |
|---|---|---|---|
| 4,893,073 A | 1/1990 | McDonald | |
| 4,922,197 A | 5/1990 | Juds et al. | |
| 4,994,738 A | 2/1991 | Soyck et al. | |
| 5,326,945 A | 7/1994 | Gotoh et al. | |
| 5,559,433 A | 9/1996 | Onizuka | |
| 5,928,227 A | 7/1999 | Howard et al. | |
| 6,356,584 B1 | 3/2002 | Cuylen | |
| 6,934,874 B2 | 8/2005 | Retter et al. | |
| 6,985,773 B2 | 1/2006 | Von Arx et al. | |
| 7,042,364 B2 | 5/2006 | Capobianco | |
| 7,099,283 B2 | 8/2006 | Matta et al. | |
| 7,197,357 B2 | 3/2007 | Istvan | |
| 7,424,288 B2 | 9/2008 | Jung et al. | |
| 7,689,169 B2 | 3/2010 | Lee et al. | |
| 7,860,456 B2 | 12/2010 | Kim | |

(Continued)

FOREIGN PATENT DOCUMENTS

| EP | 0 589 466 A1 | 3/1994 |
|---|---|---|
| EP | 2 146 431 A2 | 1/2010 |

(Continued)

OTHER PUBLICATIONS

Agrafioti et al.: On Supporting Anonymity in a Ban Biometric Framework; Digital Signal Processing, Aug. 18, 2009; © 2009 IEEE; 6 pgs.

(Continued)

*Primary Examiner* — Benjamin Lee
*Assistant Examiner* — Quang D Pham
(74) *Attorney, Agent, or Firm* — Merchant & Gould P.C.

(57) ABSTRACT

A method for automatically adding a first sensor device to a first personal area network in a healthcare application includes receiving a signal with out-of-band pairing data at the first sensor device. The first sensor device is disposed on a patient's body. The out-of-band pairing data is injected into the patient's body by a second sensor device disposed on the patient's body. Pairing data is extracted from the received signal at the first sensor device. Using the pairing data, the first sensor device is added to the first personal area.

9 Claims, 6 Drawing Sheets

(56) References Cited

U.S. PATENT DOCUMENTS

| | | | |
|---|---|---|---|
| 7,973,657 B2 | 7/2011 | Ayed | |
| 7,978,062 B2 | 7/2011 | LaLonde et al. | |
| 8,179,124 B2 | 5/2012 | De Huu et al. | |
| 2002/0008625 A1 | 1/2002 | Adams et al. | |
| 2002/0082480 A1* | 6/2002 | Riff et al. | 600/300 |
| 2003/0033032 A1* | 2/2003 | Lind et al. | 700/52 |
| 2003/0105499 A1* | 6/2003 | Hartley et al. | 607/17 |
| 2003/0142651 A1 | 7/2003 | Matta et al. | |
| 2003/0149459 A1 | 8/2003 | Von Arx et al. | |
| 2003/0206116 A1* | 11/2003 | Weiner et al. | 340/870.28 |
| 2004/0015058 A1* | 1/2004 | Besson et al. | 600/301 |
| 2004/0073127 A1* | 4/2004 | Istvan et al. | 600/513 |
| 2004/0102683 A1* | 5/2004 | Khanuja et al. | 600/300 |
| 2004/0202339 A1 | 10/2004 | O'Brien, Jr. et al. | |
| 2004/0225199 A1* | 11/2004 | Evanyk et al. | 600/300 |
| 2004/0249257 A1 | 12/2004 | Tupin, Jr. et al. | |
| 2004/0249258 A1 | 12/2004 | Tupin, Jr. et al. | |
| 2005/0068173 A1 | 3/2005 | Capobianco | |
| 2005/0097191 A1 | 5/2005 | Yamaki | |
| 2005/0251680 A1* | 11/2005 | Brown et al. | 713/171 |
| 2005/0261556 A1* | 11/2005 | Such et al. | 600/300 |
| 2006/0025834 A1 | 2/2006 | Von Arx et al. | |
| 2006/0115066 A1 | 6/2006 | Levien et al. | |
| 2006/0135065 A1 | 6/2006 | Lee et al. | |
| 2006/0179079 A1 | 8/2006 | Kolehmainen | |
| 2006/0212085 A1 | 9/2006 | Fischell | |
| 2006/0219776 A1 | 10/2006 | Finn | |
| 2006/0251256 A1* | 11/2006 | Asokan et al. | 380/270 |
| 2007/0003061 A1 | 1/2007 | Jung et al. | |
| 2007/0010748 A1 | 1/2007 | Rauch et al. | |
| 2007/0032832 A1 | 2/2007 | Feher | |
| 2007/0070035 A1 | 3/2007 | Asbury et al. | |
| 2007/0135866 A1 | 6/2007 | Baker et al. | |
| 2007/0162089 A1 | 7/2007 | Mosesov | |
| 2007/0264988 A1 | 11/2007 | Wilson et al. | |
| 2008/0005288 A1 | 1/2008 | Kodama et al. | |
| 2008/0013601 A1 | 1/2008 | Lind et al. | |
| 2008/0046039 A1 | 2/2008 | Corndorf | |
| 2008/0052132 A1* | 2/2008 | Iliff | 705/3 |
| 2008/0140160 A1 | 6/2008 | Goetz | |
| 2008/0151695 A1 | 6/2008 | Kimel | |
| 2008/0162183 A1* | 7/2008 | Sachanandani et al. | 705/2 |
| 2008/0177150 A1 | 7/2008 | Ii et al. | |
| 2008/0183245 A1 | 7/2008 | Van Oort et al. | |
| 2008/0183910 A1 | 7/2008 | Natoli | |
| 2008/0191866 A1* | 8/2008 | Falck et al. | 340/539.12 |
| 2008/0194922 A1* | 8/2008 | Holden | 600/300 |
| 2008/0227393 A1 | 9/2008 | Tang et al. | |
| 2008/0228045 A1* | 9/2008 | Gao et al. | 600/301 |
| 2008/0234557 A1 | 9/2008 | Demharter | |
| 2008/0262376 A1* | 10/2008 | Price | 600/547 |
| 2008/0281169 A1 | 11/2008 | Akkermans et al. | |
| 2008/0281170 A1 | 11/2008 | Eshelman et al. | |
| 2008/0287748 A1 | 11/2008 | Sapounas et al. | |
| 2009/0018453 A1 | 1/2009 | Banet | |
| 2009/0023391 A1* | 1/2009 | Falck | 455/41.2 |
| 2009/0030285 A1 | 1/2009 | Andersen | |
| 2009/0043531 A1* | 2/2009 | Kahn et al. | 702/149 |
| 2009/0069642 A1 | 3/2009 | Gao et al. | |
| 2009/0076343 A1 | 3/2009 | James et al. | |
| 2009/0076348 A1 | 3/2009 | Manicka et al. | |
| 2009/0076350 A1 | 3/2009 | Bly et al. | |
| 2009/0088605 A1* | 4/2009 | Ross et al. | 600/300 |
| 2009/0096573 A1* | 4/2009 | Graessley | 340/5.8 |
| 2009/0112630 A1 | 4/2009 | Collins, Jr. et al. | |
| 2009/0118595 A1* | 5/2009 | Greiner et al. | 600/301 |
| 2009/0140923 A1 | 6/2009 | Graves et al. | |
| 2009/0215398 A1 | 8/2009 | Adler et al. | |
| 2009/0222659 A1* | 9/2009 | Miyabayashi et al. | 713/156 |
| 2009/0227282 A1* | 9/2009 | Miyabayashi et al. | 455/552.1 |
| 2009/0231125 A1* | 9/2009 | Baldus et al. | 340/539.12 |
| 2009/0239587 A1 | 9/2009 | Negron et al. | |
| 2009/0275296 A1 | 11/2009 | Huang et al. | |
| 2009/0281399 A1* | 11/2009 | Keel et al. | 600/301 |
| 2009/0305212 A1 | 12/2009 | Mckenzie et al. | |
| 2009/0327713 A1* | 12/2009 | Marin et al. | 713/168 |
| 2010/0010322 A1* | 1/2010 | Brady | 600/301 |
| 2010/0010338 A1 | 1/2010 | van Dam et al. | |
| 2010/0029205 A1 | 2/2010 | Lu et al. | |
| 2010/0045425 A1* | 2/2010 | Chivallier | 340/5.8 |
| 2010/0081895 A1* | 4/2010 | Zand | 600/309 |
| 2010/0082983 A1* | 4/2010 | Shah et al. | 713/169 |
| 2010/0082990 A1 | 4/2010 | Grigorovitch | |
| 2010/0104102 A1* | 4/2010 | Brown et al. | 380/277 |
| 2010/0125188 A1 | 5/2010 | Schilling et al. | |
| 2010/0145165 A1 | 6/2010 | Merry | |
| 2010/0160742 A1* | 6/2010 | Seidl et al. | 600/301 |
| 2010/0234720 A1 | 9/2010 | Tupin, Jr. et al. | |
| 2010/0297946 A1 | 11/2010 | Alameh et al. | |
| 2011/0004072 A1* | 1/2011 | Fletcher et al. | 600/300 |
| 2011/0004073 A1* | 1/2011 | Corroy et al. | 600/300 |
| 2011/0015496 A1* | 1/2011 | Sherman et al. | 600/301 |
| 2011/0018854 A1 | 1/2011 | Barclay et al. | |
| 2011/0040345 A1* | 2/2011 | Wenzel et al. | 607/17 |
| 2011/0105861 A1 | 5/2011 | Derchak et al. | |
| 2011/0125535 A1* | 5/2011 | Gross | 705/3 |
| 2011/0137133 A1* | 6/2011 | Espina Perez | 600/300 |
| 2011/0152632 A1* | 6/2011 | Le Neel et al. | 600/300 |
| 2011/0160786 A1 | 6/2011 | Stubbs et al. | |
| 2011/0183698 A1 | 7/2011 | Hoctor et al. | |
| 2011/0208015 A1* | 8/2011 | Welch et al. | 600/301 |
| 2011/0210820 A1* | 9/2011 | Talty et al. | 340/5.8 |
| 2011/0213216 A1* | 9/2011 | McKenna et al. | 600/301 |
| 2011/0288379 A1* | 11/2011 | Wu | 600/301 |
| 2012/0001751 A1 | 1/2012 | Baker et al. | |
| 2012/0003933 A1 | 1/2012 | Baker et al. | |
| 2012/0158428 A1* | 6/2012 | Nuthi | 705/3 |
| 2012/0220835 A1* | 8/2012 | Chung | 600/301 |
| 2014/0128674 A1 | 5/2014 | Wieters | |

FOREIGN PATENT DOCUMENTS

| | | |
|---|---|---|
| JP | 61-149820 A | 7/1986 |
| JP | 4-84948 A | 3/1992 |
| JP | 2010-027611 A | 2/2010 |
| KR | 10-2009-0011863 A | 2/2009 |
| KR | 10-2009-0059324 A | 6/2009 |
| WO | WO 2006/047400 A2 | 5/2006 |

OTHER PUBLICATIONS

Chowdhury et al.: Context-aware Data Association and Authenticity in Pervasive Healthcare; Dec. 1, 2009; © 2009 IEEE Computer Society; pp. 227-230.

Falck et al.: Plug 'n Play Simplicity for Wireless Medical Body Sensors; Mobile Netw Appl, vol. 12 Issue 2-3, Jul. 25, 2007; © Springer Science + Business Media, LLC; pp. 143-153.

Olla: Mobile Health Technology of the Future: Creation of an M-Health Taxonomy Based on Proximity; Int. J. Healthcare Technology and Management, vol. 8, Nos. 3-4; © 2007 Inderscience Enterprises Ltd.; pp. 370-387.

Application filed in U.S. Appl. No. 12/827,817, filed Jun. 30, 2010.

Application filed in U.S. Appl. No. 13/225,989, filed Sep. 6, 2011.

International Search Report and Written Opinion in PCT/US2011/024853, mailed Aug. 2, 2011, 10 pages.

Antoniou et al.; "iTouch: RFID Middleware for Boosting Connectivity & Intuitive User Interaction in Smart Spaces", May 9, 2006, 34 pages.

Cho et al.; Opportunistic Medical Monitoring Using Bluetooth P2P Networks, Jun. 2008, 6 pages.

Kostelnik et al.; BlueMedica—Wireless Medical Data Access Appliance, 2008, 7 pages.

International Search Report and Written Opinion in PCT/US2012/051830 mailed Feb. 1, 2013, 10 pages.

* cited by examiner

PERSONAL AREA NETWORK PAIRING

BACKGROUND

Personal area networks in a medical setting permit sensor data from a patient to be efficiently transmitted to a display device. These networks typically use Bluetooth technology both in sensors attached to the patient and in the display device. Each Bluetooth sensor is typically paired to the display device to enable the transmission of sensor data to the display device.

The pairing of Bluetooth sensors in a personal area network generally requires input from a user and requires the user to execute many keystrokes. In a medical setting, the pairing also requires that patient be uniquely identified to ensure that sensor data being transmitted in the personal area network is associated with the correct patient.

SUMMARY

Aspects of the disclosure are directed to automatically adding a first sensor device to a first personal area network in a healthcare application. A signal with out-of-band pairing data is received at the first sensor device, the first sensor device disposed on a patient's body. The out-of-band pairing data is injected into the patient's body by a second sensor device disposed on the patient's body. Pairing data is extracted from the received signal at the first sensor device. Using the pairing data, the first sensor device is added to the first personal area network.

In another aspect, a first sensor device in a first personal area network in a healthcare application is re-identified. The first sensor device is placed on a patient's body, the first sensor device being included in the first personal area network. The first sensor device is then removed from the patient's body. The removing of the first sensor device from the patient's body disconnects the first sensor device from the first personal area network. After the first sensor device is removed from the patient's body, the first sensor device is re-attached to the patient's body. The re-attaching of the first sensor device to the patient's body reconnects the first sensor device to the first personal area network.

In yet another aspect, an automatic determination is made whether physiological sensors are detecting physiological data from the same patient. A first sensor device is placed on a patient's body, the first sensor device adapted for joining a first personal area network. A second sensor device is placed on the patient's body, the second sensor device adapted for joining the first personal area network. First physiological data from the patient's body is measured using the first sensor device. Second physiological data from the patient's body is measured using the second sensor device. The first and second physiological data of the first and second sensor devices are correlated. A determination is made whether the first and second sensor devices are associated with the same patient based on correlation of the first and second physiological data.

In yet another aspect, a patient is automatically identified in a healthcare application. A wristband is attached to a patient, the wristband adapted to provide out-of-band pairing data. A sensor device is coupled to the wristband. The sensor device detects the out-of-band pairing data. The sensor device is attached to the patient's body. A personal area network is detected that uses the detected pairing data. The sensor device joins the personal area network that uses the detected pairing data.

In yet another aspect, the names of patients proximal to a detector are discovered and displayed. A detecting device is provided to a user for discovering one or more personal area networks. Each of the one or more personal area networks has a unique network identifier. At the detecting device, one or more personal area networks are discovered. The network identifier is obtained for each of the one or more personal area networks that are discovered at the detecting device. For each obtained network identifier, one or more patient identifiers are obtained that are uniquely associated with the obtained network identifier. A list of the obtained patient identifiers is displayed.

The details of one or more techniques are set forth in the accompanying drawings and the description below. Other features, objects, and advantages of these techniques will be apparent from the description, drawings, and claims.

DETAILED DESCRIPTION

The present disclosure is directed to systems and methods for pairing physiological sensor devices for a patient in a personal area network (PAN).

A personal area network is a computer network used for communication between computer devices close to an individual person. A PAN may also be referred to as a Body Area Network (BAN) when the PAN is a collection of physiological sensors and monitors. In this disclosure, "pairing" refers to Bluetooth pairing and also to equivalent transmission of authentication credentials, such as public keys and nonces that may be used to authenticate devices for secure, authenticated data transfer.

In a medical setting, a personal area network may include physiological sensor devices attached to a patient that are used to monitor health parameters of the patient. Some examples of physiological sensor devices used in a medical setting are blood pressure monitoring devices, thermometers, ECG sensors, EEG sensors, cardiac output sensors, $ETCO_2$ sensors, and oxygen saturation sensors. Other types of sensor devices can be used. The sensor devices typically transmit sensor data over a network to a patient monitoring device, such as a wall-mounted display unit or a central station, such as the Welch Allyn Acuity Central Station.

One type of personal area network is a wireless personal area network. In a wireless personal area network, sensor data is transmitted using a wireless data exchange protocol, such as Bluetooth to a central point, called a hub. Often, this central point has a connection to a larger network, such as an 802.3 or 802.11 LAN. A cellular phone might have a connection to a cellular Wide Area Network and an 802.11 LAN. A hub with a connection to a different type of network is called a bridge.

In a wireless personal area network for monitoring sensor data, each sensor device may be joined to the network. In Bluetooth (BT), joining a network when none of the network information (link key or BT_ADDR of the other network members) is known requires pairing. While this disclosure uses BT as an example PAN, any network, including 802.15.4, ZigBee, UWB, a low-power 802.11 network, or a proprietary network could be used. A hub to which multiple sensors are paired that includes a display to show the physiological state of the patient is a patient monitoring device. This type of hub typically has a local area network uplink, making the patient monitoring device a bridge. The appropriate pairing of a sensor device with a patient monitoring device ensures that the sensor data is properly transmitted to the correct monitoring device. This is particularly important in a medical setting that may include a plurality of patients, sensors, monitoring devices and personal area networks.

The procedure for pairing a sensor device to a monitoring device typically requires a user to manually enter data in order to complete the pairing. For example, a user at the monitoring device may need to manually enter an identification number (ID) for the sensor device and may need to enter a patient's ID (PID) and other information. The systems and methods described in the present disclosure permit sensor devices to be attached to a patient and paired to a monitoring device in an efficient and automated manner, thereby minimizing the need for a user to manually enter information.

One type of sensor device used in a wireless personal area network is a Bluetooth sensor. Bluetooth is a wireless technology that can be used in personal area networks to transmit and receive data over short distances (generally less than 30 feet, although data can be transmitted up 100 meters depending on device class). Bluetooth uses a layered protocol architecture consisting of four core layers and associated protocols. The lowest layer in each Bluetooth device is a radio frequency ("RF") layer that includes a transceiver with transmit and receive capability. This lowest layer is sometimes referred to as a Bluetooth radio. Bluetooth uses the microwave radio spectrum in the 2.402 GHz to 2.4835 GHz range.

Bluetooth devices are peer devices, each including a Bluetooth radio and the four core protocol layers. However, when two or more Bluetooth devices are connected in a personal area network, one device can become a master device and the remaining devices then become slave devices. A master Bluetooth device can communicate with up to seven slave devices. However, a slave can switch roles and become a master at any given time. A Bluetooth device may be a slave in one PAN and a master in a second PAN.

Because Bluetooth is a wireless technology, security is a concern. To improve security, Bluetooth permits two devices to be paired with each other so that they can securely communicate with each other. Once two devices are paired, they can communicate with each other without user intervention. The pairing process is typically initiated the first time a device receives a connection request from a device to which it is not already paired. During the pairing process, a shared secret, known as a link key or a Bluetooth key, is shared between the two devices. The link key is used during each communication between the two devices to ensure the integrity of the communication.

Bluetooth permits several pairing mechanisms. One pairing mechanism (introduced in Bluetooth Version 2.1+EDR) is Secure Simple Pairing (SSP). SSP has four modes of operation: Numeric Comparison, Passkey Entry, Just Works, and Out-Of-Band (OOB). With the first two modes, some degree of user intervention is required, typically to enter manually enter device identification information. In the third mode, the devices assume that a user authentication step occurred and opens the device to a security risk, such as a man-in-the-middle (MITM) attach. The OOB mode described herein permits two devices to be paired simply by placing the two devices on the same patient. OOB pairing uses an external means of communication (outside of the normal 2.4 GHz Bluetooth physical layer) to exchange information in the pairing process. Typical information exchanged using OOB pairing includes the device ID and the Bluetooth link key. Other uses of OOB communication are possible.

Figure 1:
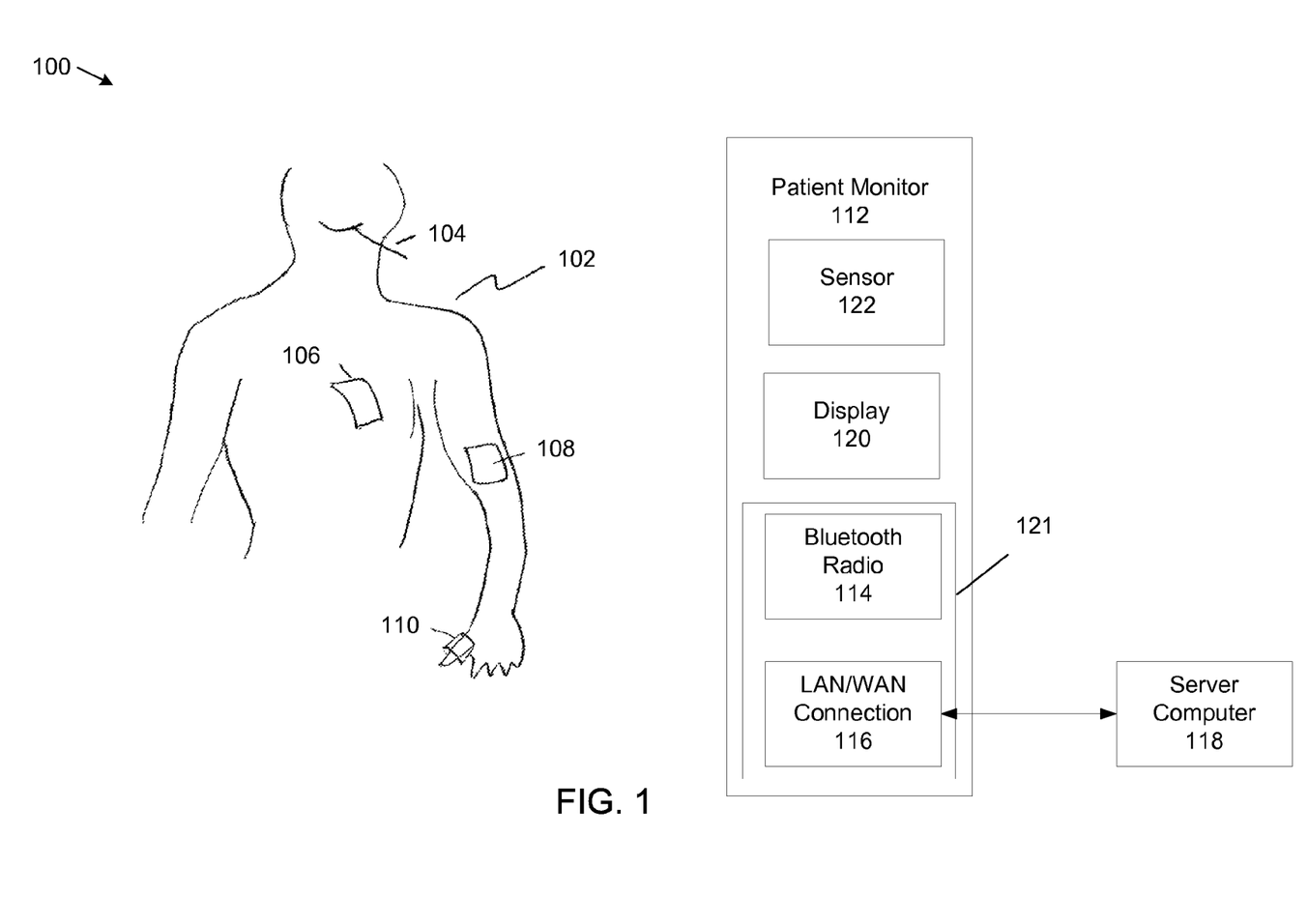
FIG. 1 shows an example personal area network used in a medical application.

FIG. 1 shows an example personal area network 100 used in a medical application. The example personal area network 100 includes a patient 102, four example physiological sensors 104, 106, 108, 110 and an example patient monitor 112. The four physiological sensors include an example thermometer 104, ECG sensor 106, blood pressure sensor 108 and $SPO_2$ sensor 110. The $SPO_2$ sensor is also known as an oxygen saturation sensor.

Each of the example physiological sensors 104, 106, 108, 110 has Bluetooth capability and, therefore, all include a Bluetooth radio. The example patient monitor 112 includes a Bluetooth radio 114 and a LAN/WAN connection 116, providing a gateway 121. The LAN/WAN connection 116 permits data to be transmitted between the example personal area network 100 and one or more server computers 118 that are accessible via the LAN/WAN connection. The patient monitor 112 also may include one or more embedded sensors 122 that have a physical attachment to patient monitor 112. In addition, the patient monitor 112 includes a Bluetooth Radio 114, and a display 120 that indicates the state of various sensors and network connections.

In the example personal area network 100, one of the physiological sensors 104, 106, 108, 110 is paired to patient monitor 112 using one of the Bluetooth pairing methods described above. This establishes the personal area network 100 between the physiological sensor and patient monitor 112. Alternately, a sensor that has a physical attachment to patient monitor 112, such as embedded or wired sensor 122, may establish the personal area network 100. In either case, a sensor on the patient has access to the Bluetooth radio 114.

Once the personal area network 100 is established, each additional physiological sensor is automatically paired to patient monitor 112 simply by attaching the additional physiological sensor to the body. The user need not supply additional configuration or authentication. This automatic pairing is achieved by using the body as the medium for passing Near-Field Communication (NFC) data using Bluetooth OOB pairing. Similar solutions may be used for other, non BT networks. In OOB pairing, the pairing and security information that are transmitted across the OOB link may be the same as are transmitted across the BT link using the other three secure simple pairing methods: numeric comparison, just works, and passkey entry.

BT may use both uni- and bi-directional authentication and OOB pairing to create a secure link. This document also indicates the OOB information may be transmitted before or after initiating the BT connection. Two categories for OOB task flows can include: 1) activating the OOB mechanism and subsequently initiating the Bluetooth pairing process; and 2) initiating the Bluetooth connection (no pairing) and subsequently exchanging OOB information for authentication. Either of these may be used.

There are two broad OOB implementations supported by BT Secure Simple Pairing: bi-directional and uni-directional.

For bi-directional implementations, one example involves two devices that are physically brought together and the Bluetooth Secure Simple Pairing information is passed via the NFC channel, thus initiating the Bluetooth Secure Simple Pairing process. The task flow may also be used with two devices equipped with a complementary mechanism for physically passing the Bluetooth Secure Simple Pairing information via a cable or other digital file transfer media.

For uni-directional implementations, the unidirectional task flow is used to capture all scenarios where two devices are equipped with the same mechanism for transferring Bluetooth Secure Simple Pairing information via an OOB channel but where the information is passed only in one direction. For some unidirectional task flows, the OOB initiator sends the Bluetooth Secure Simple Pairing information to the OOB responder (i.e. via an email, file, token, etc.). Since this information is not explicitly acknowledged by the OOB responder, the OOB initiator then becomes the Bluetooth Responder as the OOB responder initiates the Bluetooth Secure Simple Pairing process. Applications can be used to handle the OOB information. Such examples are a Short Message Service (SMS) or email with the configuration information listed that the device can use.

In a first implementation, the body-medium is used for bi-directional BT pairing. In a second implementation, the body-medium is used for uni-directional authentication.

Using the body for the medium for NFC and Bluetooth OOB pairing requires that the first physiological sensor paired to patient monitor 112 provides an electrical or RF connection to the body. Alternately, embedded sensor 122 may provide this electrical or RF connection to the body and is considered the first physiological sensor.

In some examples, the devices need not be physiological sensors. As an example, the first "sensor" could support the radio and the OOB function and have no actual physiological sensor. The example ECG sensor 106 inherently has the ability to provide a low-impedance electrical connection to the body, allowing it to easily be adapted to inject a modulated signal into the body that may be detected by other body-worn sensors. Some other physiological sensors may need to be modified to provide an electrical or RF connection to the body.

For example, it is possible to add a metal foil to the cuff of example blood pressure sensor 108 to provide low-impedance connectivity to the body. Similarly, it is possible to add a small metal contact in the fingertip or forehead probe of example SPO$_2$ sensor 110. Often, metal surfaces are avoided due to ESD concerns. In lieu of a metal surface exposed to the environment and touching the body, an antenna that is insulated could be used. A conducting strip inside the NIBP cuff would serve as a loop antenna around the arm or leg and the metal tip of an electronic thermometer would serve as a dipole antenna. Loop antennas could be placed also inside of SPO$_2$ and other sensors.

Once the first physiological sensor, for example ECG sensor 106, is paired to patient monitor 112, this sensor injects a low current AC signal into the body. The existence and detection of this signal may be used for OOB discovery, after which BT information for personal area network 100 is transmitted over the OOB link by modulating the low current AC signal with the binary information. Next, the connection is established using BT Page (but over the OOB link). Public keys are exchanged over the OOB and 6-digit confirmation codes are derived and optionally presented (as appropriate for the selected BT pairing & association model). Finally, authentication (e.g. comparing the 6-digit confirmation codes) occurs. For Just Works, the comparing of 6-digit confirmation codes authentication step is effectively omitted. BT Just Works is subject to Man-in-the-middle (MITM) attacks, but by using the patient's body as the communication medium, MITM is mitigated and therefore a secure solution may be achieved using "Just Works." That is, authentication may occur automatically as each device knows that the other is attached to the same person and therefore rightfully should belong to the same PAN. In this solution, both BT devices need transceivers capable of communicating via the human body as most or all of the bi-directional transactions that normally occur over BT for Secure Simple Pairing occur over the OOB channel.

Alternately, the BT pairing may occur over the BT link and the authentication occurs by detecting the devices are on the same body. Detecting the devices are on the same body may also be used for OOB discovery. Detecting the devices are on the same body may include each device transmitting and the other device receiving a pre-defined signal. This pre-defined signal could range from a simple ping to show both devices are on the same body to exchange and comparison of the 6-digit confirmation code via the body medium. The discovery signal and the authentication signal might be the same and implemented in one step or they might be different and implemented in different steps. Devices may also determine they are on the same body through correlation of physiological signals or correlation of noise (e.g., muscle artifact) signals as described in this specification.

In another implementation, one device could transmit authentication signal and the other device would receive and verify these signals. This could be a simple ping, or the 6-digit BT confirmation code. Using the 6-digit confirmation code could be accomplished in a solution analogous to passkey entry. In passkey entry, useful when one device has a data entry method and a second has a display, each device computes the 6-digit confirmation code. The device with a display shows the code and the user enters that code on the keyboard. The device with the keyboard compares the entered code to the one that was computed, and if the same, authentication is established. In the present invention, the step of the user reading and entering the 6-digit confirmation code is automated by transmitting it through the body. Each device computes the 6-digit confirmation code. One device transmits it using OOB (analogous to showing the 6-digit confirmation code) and the other device receives it via OOB (analogous to user entry of the 6-digit confirmation code).

In all these OOB solutions, either OOB or BT may be activated first, by either: 1) activating the OOB mechanism and subsequently initiating the Bluetooth pairing process; or 2) initiating the Bluetooth connection (no pairing) and subsequently exchanging OOB information to complete the pairing. OOB BT pairing information is the information required by one of the methods described to be transmitted out of band to accomplish BT pairing. Discovery includes BT discovery and similar processes by which a device may determine another device with which it may connect is in proximity.

Continuing with the description of FIG. 1, when a second physiological sensor is attached to the body, for example blood pressure sensor 108, the second physiological sensor detects the modulated OOB signal, demodulates the signal and extracts the OOB BT pairing information. As described above, this might be the full pairing information, a derived confirmation code, or a simple ping to show connection to the same body for OOB discover, depending on the implementation. The OOB BT pairing information is then used, possibly with other information transmitted over the BT link, to pair the second physiological sensor with patient monitor 112. Any additional physiological sensors attached to the body can also detect the modulated signal, extract the OOB BT pairing information and become paired with patient monitor 112 in the same manner. As a result, personal area network 100 includes a plurality of physiological sensors attached to a patient's body, each physiological sensor being paired to patient monitor 112.

The low current AC signal that is injected into the body has a range of 50 to 300 microamperes peak to peak and is typically about 100 to 200 microamperes peak to peak. The signal is generated internally by the physiological sensor that injects the signal. Each physiological sensor includes a battery to power the Bluetooth circuitry and the OOB circuitry appropriate for the implementation. Some implementations described require an OOB transceiver on each sensor while others require a transmitter on one device and a receiver on all the others. Each physiological sensor may also include circuitry to generate the low current AC signal from the battery.

Each of physiological sensors 104, 106, 108, 110, 122 may include circuitry that provides for modulating the low current AC signal with the OOB BT pairing information and that provides for demodulating the detected signal to extract the OOB BT pairing information. Any modulation scheme may be used. For example, if amplitude modulation (AM) is used, a carrier, typically in the 40 to 60 kHz range, is modulated by the OOB BT pairing information, the envelope of the modulated signal carries the data. An example simple AM modulator can be constructed using a FET (field-effect transistor) as a voltage variable resistor that is input to an operational amplifier. The OOB BT pairing information modulates the gate of the FET, modulating the resistance of the voltage variable resistor input to the operational amplifier, causing a variation in gain. If the input signal to the operational amplifier is a sinusoidal signal (this is the carrier), the output of the operational amplifier is the carrier amplitude modulated by the OOB BT pairing information that is driving the gate of the FET. Other modulation scheme examples are possible.

Each of example physiological sensors 104, 106, 108, 110, 122 typically includes an antenna that is used to detect the modulated signal. To protect against interference from other signals that may be detected by the antenna, the Bluetooth data may be encoded using an error correction scheme, for example forward error correction. A low-impedance connection to the body from the device that injects the AC signal on which the OOB BT pairing information is modulated also provides a degree of protection from external interference as external signals would poorly couple to the human body. Some additional methods of protecting against interference include a direct sequence spread spectrum (DSSS) modulation technique, using and ACK/NACK protocol, or simply transmitting the modulated signal repeatedly and integrating the results. Other protection schemes are possible.

The physiological sensor that injects the modulated AC signal into the body, for example ECG sensor 106, may continually inject the signal into the body or may inject the signal into the body at a predetermined time interval. If the signal is injected continuously, any new sensor attached to the body can immediately detect the signal. However, this has a cost of higher power. If a duty cycle less than 100% is selected, the power cost is lower, but the detection time may be longer. For example, if the injected signal takes 10 ms to transmit, but the signal is injected into the body only once per second, a new sensor added to the body may need to wait as long as one second in order to detect the signal.

Once the example personal area network 100 is created in the manner described (i.e. by pairing a first physiological sensor to patient monitor 112 and then attaching additional physiological sensors to the body), data can be transmitted from each of the physiological sensors to patient monitor 112. Sensor data is transmitted through the air via Bluetooth to patient monitor 112 via Bluetooth radio 114. Each transmission of sensor data may include the patient ID (PID) in order to ensure that the data is being transmitted from the correct patient. Each physiological sensor obtains the patient ID number from the personal area network 100. The PID may be obtained directly from a server (e.g. server 118) that is accessible via LAN/WAN connection 116 or the patient ID may be obtained from another physiological sensor or patient monitor 112 that may have already obtained the patient ID from a server. Alternately, since the sensor 102, 104, 106, 108, 110 is paired to exactly one patient monitor 112, then the physiological data might be transmitted from the sensors to patient monitor without the PID and the patient monitor 112 appends the PID number to the data.

Figure 2:
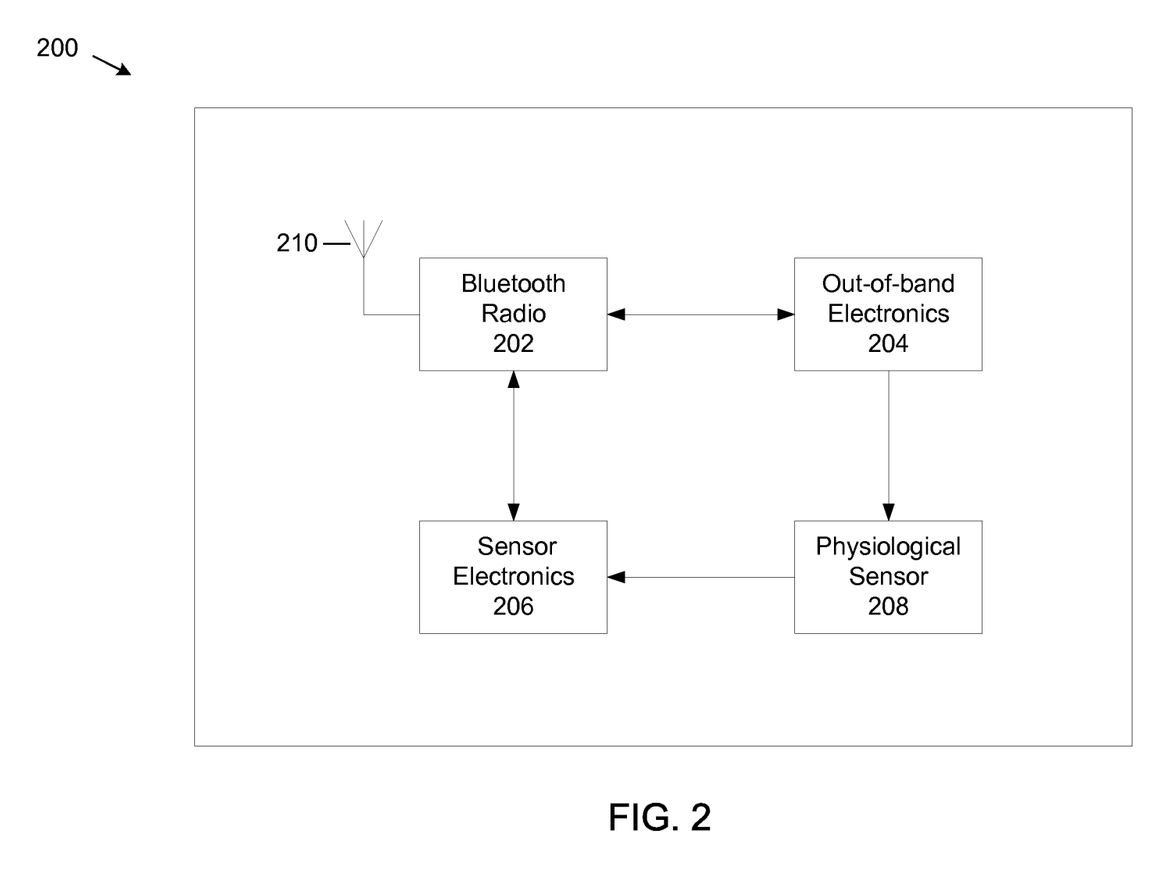
FIG. 2 shows example modules of a Bluetooth physiological sensor device having an out-of-band pairing capability.

FIG. 2 shows a block diagram of an example Bluetooth physiological sensor module 200 having an OOB pairing capability. The example sensor module 200 includes an example Bluetooth radio 202 with example antenna 210, example OOB electronics 204, example sensor electronics 206, and an example physiological sensor 208. The example physiological sensor 208 may be a thermometer, ECG sensor, blood pressure sensor, SPO$_2$ sensor or any other similar physiological sensor. Example sensor 200 shows a sensor that is adapted to transmit and receive OOB BT pairing information through the physiological sensor 208.

When the example physiological sensor 208 is the first sensor attached to the body and is paired with a patient monitor, for example patient monitor 112, the example OOB electronics 204 modulates a low-current AC signal with OOB BT pairing information and sends the modulated low-current AC signal to the example physiological sensor 208 for injection into the body. The OOB electronics includes circuitry that produces the low-current AC signal from a DC power source, typically a battery in the example sensor module 200. The modulated low-current AC signal may be continually injected into the body or may be injected into the body periodically. Example physiological sensor 208 can determine if it is the first sensor attached to the body by attempting to receive OOB BT pairing information. If OOB BT pairing information is detected, the sensor does not modulate and inject a low-current AC signal with OOB BT pairing information.

When the example physiological sensor 208 is not the first sensor attached to the body and is not already paired with a patient monitor, the modulated low-current AC signal injected into the body by the first sensor attached to the body is detected through physiological sensor 208 and processed by OOB electronics 204. The OOB electronics 204 demodulates the detected signal and extracts the OOB BT pairing information. The OOB provides the BT pairing information to Bluetooth Radio 202 to connect to a patient monitor and pair this physiological sensor to the patient monitor as described elsewhere in the specification.

Once a physiological sensor is included in a personal area network, for example personal area network 100, and paired to a patient monitor, sensor data from example physiological sensor 208 is sent to example sensor electronics 206, Bluetooth radio 202 and antenna 210 and transmitted to the patient monitor 112.

A personal area network for a medical application can also be used to determine when sensors are on the same patient from correlation of physiological data. Any signals that may be detected by at least two sensors can be used for this method. Some specific, but not limiting, examples are now described. Several of the example physiological sensors shown in FIG. 1 can be used to measure common physiological data. For example, ECG sensor 102, blood pressure sensor 103 and $SPO_2$ sensor 104 can all measure heart rate. One aspect of heart rate is the heart rate variability, or beat-to-beat interval. If the beat-to-beat intervals of the heart rate as determined by example sensors 102, 103 and 104 are correlated, it confirms that example sensors 102, 103 and 104 are all on the same person. As another example, ECG-detected respiration rate and periodicity of $ETCO_2$ (end-tidal carbon dioxide, the level of carbon dioxide released at the end of respiration) signals are also highly correlated.

In addition, respiration may modulate a patient's heart rate and/or the pulse amplitude, so it may be possible that any device that detects heart rate can correlate data with a sensor that detects respiration. Respiration could be measured using example blood pressure sensor 103, example ECG sensor 106, and $ETCO_2$ sensor (not shown). Respiration may be detected by examining pulse amplitude and momentary pulse-rate depression via example NIBP sensor 108; ECG sensor 106 detects respiration using impedance pneumography; periodicity of the $ETCO_2$ signal (respiration rate) can be measured using either a side-stream or main-stream sensor (not shown). If the occurrences of detected breaths are correlated, the correlation confirms that example sensors 103 and 106 and $ETCO_2$ (not shown) are all on the same person.

As discussed later in the specification, determining the exact level at which one defines a positive correlation as a "true positive" or the exact level at which one defines a low correlation as a "true negative" can be difficult due to phase differences between the signal detected by different physiological sensors and also a varying phase difference. Sensors from different manufacturers will have different phase, noise, and signal characteristics, so the proper levels can be determined through laboratory testing and clinical trials.

However, by way of example, consider a single triangular pulse of duration 167 ms sampled at 60 Hz with a heart rate of 1 Hz and sample duration of 12 seconds. If both sensors detect the same signal in phase, the correlation factor is one. If the second data set is offset by a single sample (1.6 ms), the correlation factor decreases to 0.93. Assuming one-sample timing resolution, requiring a correlation of higher than 0.93 to call a "positive" will result in many false negatives (that is, deciding that the sensors are on different patients when they are on the same patient) as 0.93 is realistically the best correlation factor. If in addition, there is a +/−1 sample jitter between samples (perhaps due to vascular contraction/dilation), then the correlation factor decreases to 0.89. With testing, the amount of jitter can be quantified and using this information, a bound set for what correlation factor will be called a "positive" meaning the sensors are determined to be on the same patient.

Now considering the case of sensors on different patients, if the second data set is from a different patient with a heart rate of 0.98 Hz (one additional sample between the pulses), then if the first beat is synchronous between the two sensors, the correlation for the entire data set is 0.25. If the data set is decreased to 3 beats, then the correlation for the shorter data set is 0.81. Therefore, the longer the data set, the stronger the statistical strength in the correlation coefficient. Assuming 12 seconds and 12-beats, a correlation of 0.25 or lower could be called a "negative", meaning the sensors are determined to be on different patients.

The value of correlation coefficient determined to indicate a "positive" or a "negative" might be dynamically modified based on the number of sensors in the system, the amount of system noise, and the sample size provided the correlation algorithm.

Typically, each sensor sends physiological data via Bluetooth to patient monitor 112 and patient monitor 112, in turn, sends the physiological data to server computer 118 via LAN/WAN connection 116. The server computer 118 or patient monitor 112 includes software that correlates the physiological data. For example, if the physiological data measured is the heart rate of a patient, application software on the server computer determines the beat-to-beat interval of the heart rate. The beat-to-beat interval measured by a plurality of sensors is correlated to verify that the sensors are all on the same patient. Alternately, the patient monitor 112 or any other computing device, including the sensors themselves, may perform the correlation.

Physiological sensors may be reused so that after sensor data is obtained from one patient, the same sensor may be used at a later time for another patient. When a sensor is reused in this manner, it must be ensured that the PID of the previous patient is not used for the next patient. Therefore, when a sensor is removed from a patient, the PID data link for the sensor is broken. When a previously used sensor is reattached to a new patient, the sensor determines whether it is on the same patient or a different patient by one of the mechanisms discussed previously. That is, using a PID that is modulated onto a low current AC signal that is injected into the body, or using a correlation of physiological data from different sensors. Additionally, a clinical input may accomplish this same function of breaking the PID to data link for the sensor.

As stated above, when a physiological sensor is removed from a patient, the PID to data link for the sensor is broken. Typically, when a physiological sensor is attached to the patient, the physiological sensor can detect this by a continuous physiological input. Additionally, the sensor could periodically determine if it can detect a modulated AC signal or a physiological sensor may periodically attempt to correlate physiological data, such as heart-beat variability. When a physiological sensor is removed from the patient, the next periodic confirmation that the sensor is attached to the body will fail, providing an indication that the sensor has been removed from the body. Other means of breaking the PID data link for a sensor are possible. For example, the PID to data link for a sensor may be terminated when the Bluetooth connection is broken or upon a user command.

When a sensor has been temporarily removed from a patient, perhaps for a shower or because it fell off, the physiological data correlation may be used to determine if the sensor was correctly returned on the original patient. If it was correctly returned to the original patient, a sensor that has the PID stored, could again tag the physiological data with the PID. A sensor that was part of a PAN could automatically re-join the PAN without need for a clinical confirmation. Conversely, if the sensor detects it was not placed on the original patient, sensor can transmit to an equipment alert providing this information to a clinician via a gateway, PDA, or other computing device.

Figure 3:
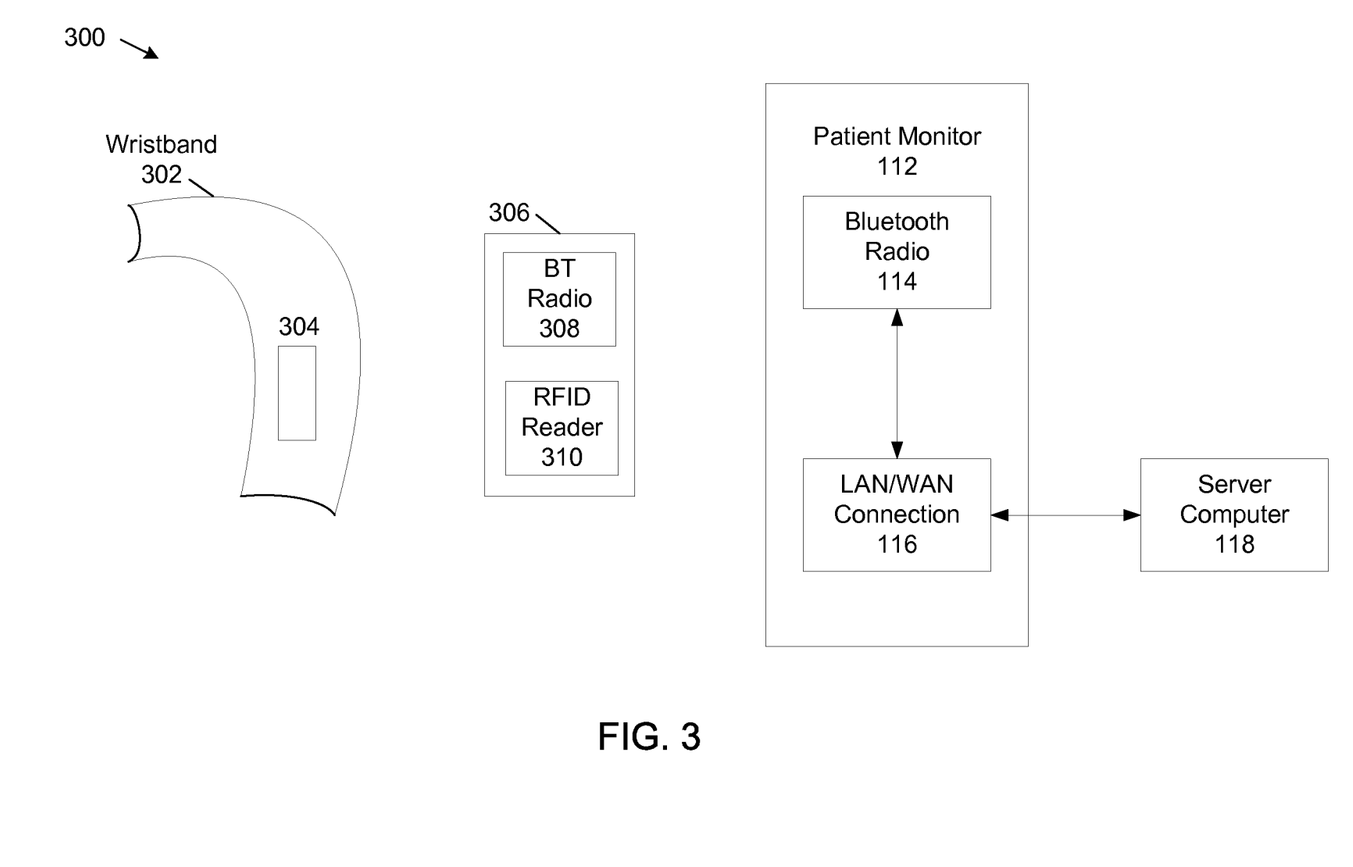
FIG. 3 shows a drawing of an example wristband having an example RFID device and an example sensor having a Bluetooth radio and an RFID reader.

Referring now to FIG. 3, a sensor may also be added to a personal area network using a patient wristband. When a patient enters a hospital, the patient is typically given a wristband to wear that contains personal information for the patient. Personal information may include the patient's name, address, PID, current medications, known allergies, etc. It is common for the PID to be encoded into a bar code imprinted on the wristband. A hand-held bar code reader can then be used to read the bar code and display patient information on a monitor screen. Alternatively, an RFID device may be used instead of a bar code. An RFID reader can then be used to read the patient information from the RFID device.

FIG. 3 shows an example wristband 302 having an example RFID device 304. FIG. 3 also shows an example Bluetooth sensor device 306 with Bluetooth radio 308 and RFID reader 310 and example patient monitor 112 that includes Bluetooth radio 114 and LAN/WAN connection 116 to server computer 118. When the example RFID device 304 is used in the example wristband 302 to provide patient information, if the Bluetooth sensor device 306 is proximal to the RFID device 304 on the wristband, both the PID and Bluetooth pairing information are transferred to the Bluetooth sensor device 306. The PID and Bluetooth pairing information are transferred to the wristband 302 using the Bluetooth OOB pairing mode which permits Bluetooth devices to be paired. The OOB discovery is accomplished when the RFID is read. In an alternate embodiment, the RFID contains only one of PID and OOB BT pairing information. If only PID is contained, then the OOB mechanism accomplishes confirmation/authentication that the new device belongs on the same network as the other BT devices on the same patient. If only OOB BT pairing information exists, then pairing as described above of injecting a low-current AC signal with uni-directional authentication may occur.

Once the Bluetooth sensor is paired in this manner, the Bluetooth sensor device 306 can be placed on the patient and sensor data can be transferred to the patient monitor 112. The use of a PID wristband with RFID therefore permits a Bluetooth sensor to obtain a PID and pairing information from a single action—placing the Bluetooth sensor near the wristband.

In a medical setting (for example a hospital or clinic), a plurality of Bluetooth networks may exist that obtain physiological sensor data from a patient. A hospital or clinic employee can use a hand-held electronic device such as a personal digital assistant (PDA) having Bluetooth capability to detect one or more proximal PANs if the PDA and a gateway on a proximal PAN are both in discoverable mode. An application on the PDA, upon request from the user to discover local networks, may contact the gateway via a LAN/WAN connection and cause the gateway to enter discoverable mode. At the same time, the application on the PDA causes the PDAs BT radio to enter discoverable mode. This allows the PDA to discover the proximal PANs, including the BT device address of each PAN's gateway. If the PDA, or a networked device available to the PDA, has a mapping of the BT device address (BT_Addr) to PIDs, then this mapping may be compared against the PANs discovered in BT discovery to provide a patient list of the proximal patients. The clinician is then provided a list of only those nearby patients instead of the entire patient list.

As an alternative to detecting proximal personal area networks, the PDA device can be used to obtain from the server the room number in which the patient is located. The server can then determine from the room number, the patients in rooms of close proximity and display on the PDA a patient list consisting of only the nearby patients.

If the functionality of OOB is significantly superior to Just Works, the extra cost of OOB may be preferable. For example, if clinician keystrokes at sensor 108 and patient monitor 112 are completely eliminated while still providing a positive confirmation of the PID to bind with the physiological data. Using a solution similar to impedance pneumography, one can modulate the pairing information onto an AC signal and use the body as the communication medium. In impedance pneumography, the patient's respiration rate is determined by detecting on one side of the thoracic cavity a low-current AC signal injected into the other side of the thoracic cavity. The change in size/shape of the thoracic cavity due to movement of the diaphragm modulates the injected signal, allowing the detector to determine a respiration rate. Similarly, a first device, attached to the patient's body, could inject the OOB data such as Discovery, Security Information and BT Address, as disclosed in the BT Core V2.1+EDR specification.

A second device could detect and demodulate the signal, then transmit a response, according the same OOB communication method that might be used for IrDA and is known to those skilled in the art. The devices might begin transmitting based on initial power-on, a button press, or upon attachment to the patient's body. EEG and ECG have direct electrical contact to the patient body. Other sensors would need to be adapted to detect and inject the modulated signals. For example, and NIBP cuff might have a conductive wire that forms a loop when the cuff is attached to the patient's arm. An electronic thermometer typically has a metal tip and this tip is usually covered in a thin plastic sheath for infectious control, so direct electrical contact does not occur. The metal tip could be used as a short-dipole antenna. Similarly, many other physiological sensors could be adapted to transmit and receive the OOB data transmitted through the patient body.

An advantage of using a body as the OOB communication medium for pairing information and authentication credentials is that there is essentially no transmission except through the body. This means that any two devices that pair are known to be on the same patient and therefore clinical confirmation of the correct binding of PID to device is no longer required. After the first sensor is applied with a PID, binding of the PID to the physiological data may then be automatic.

An alternate method to automatically bind the PID to the physiological data is through the correlation of physiological signals. As an example, the clinician may attach a patient monitor that includes an ECG sensor and subsequently attach an SPO2 sensor that uses BT Just Works association. As described previously, using Just Works without benefit of a confirmation of PID to sensor binding, could lead to sensors that automatically pair, measure physiological data and transmit that data, with the incorrect PID. However, if a first sensor is attached to a patient and measuring physiological signals then a second sensor on the same PAN is subsequently attached to a patient and the physiological data are correlated, then it can be inferred that the first and second sensor are attached to the same patient. In this scenario, either both sensors are paired to the same gateway OR a sensor is wired to the gateway and the second is paired to the gateway.

In either case, one sensor is known to have a correct PID-to-physiological-data binding and a new sensor is being added. This new sensor pairs to the PAN gateway and transmits data to the gateway, but the gateway initially does not forward the data to the server. Instead, the gateway determines the correlation factor between the two data sets and if the correlation factor is high enough, for example greater than 0.8, then the system may automatically bind the PID to the physiological signal. Conversely, with a low enough correlation factor, a system might query the clinician to confirm the PID is correctly bound to the physiological data and/or to make adjustments to reduce the system noise. The query to confirm PID could serve as a safeguard in case the clinician moved a wireless sensor from a first patient and a first patient monitor to a second patient while leaving the sensor paired to the first patient monitor. If the correlation coefficient is very low and the two sensors are on the same patient, then there may be noise, perhaps due to motion artifact or poor electrode preparation, which should be corrected.

Quantifying the correlation between two different physiological signals can be impacted by large temporal lags those signals. For example, the R-wave of the normal sinus rhythm may precede by a full second the associated radial pulse detected by an NIBP sensor. For a heart rate of 120 BPM, this would put the radial pulse 2 beats behind the electrical cardiogenic signal. To properly determine the peak correlation, data should be correlated using the radial pulse that is due to the matching electrical cardiogenic signal. As such, the correlation algorithm may implement a time window over which it assesses the correlation. By changing the offset in time between the start of the two data sets, a peak in the correlation will occur at the offset (in the example, 2 beats) between the two beats. In addition, there may be some jitter on the phase difference between the two physiological signals of a few degrees from beat to beat and the correlation algorithm needs to be able to determine a correlation coefficient in presence of jitter. As more sensors are added to the network, multi-signal digital signal processing can be used to gain higher confidence in the correlation coefficient.

Correlation of non-physiological data can also be used to determine when sensors are on the same patient. A physiological signal is typically comprised of two components. The first component contains the information desired by the clinician. The second component consists of what can be considered noise for that parameter, but is still physiological in the sense it the "noise" was generated by the patient's body. The noise can be caused by such things as physical movement (e.g. patient motion, shivering, jostling from an ambulance ride or from applying a sensor) or undesired physiological components (e.g. breathing artifact in NIBP sensor 108). Often this noise data is evident on more than one physiological sensor and can be used to correlate two parameters to the same patient. For example, flexing of the abdominal muscles, as would occur when a patient coughs or moves, is clearly evident on ECG sensor 106, $SPO_2$ sensor 104 and NIBP sensor 108 as shown in FIG. 1. Such gross muscle movements would be unlikely to happen on two patients simultaneously, and could be used to both confirm correct pairing and flag incorrect pairing. Another example would be when not one large muscle movement occurred, but several smaller movements occurred. Spacing between the motion events should remain consistent across parameters, and motion event relative amplitude is likely to remain consistent as well.

Figure 4:
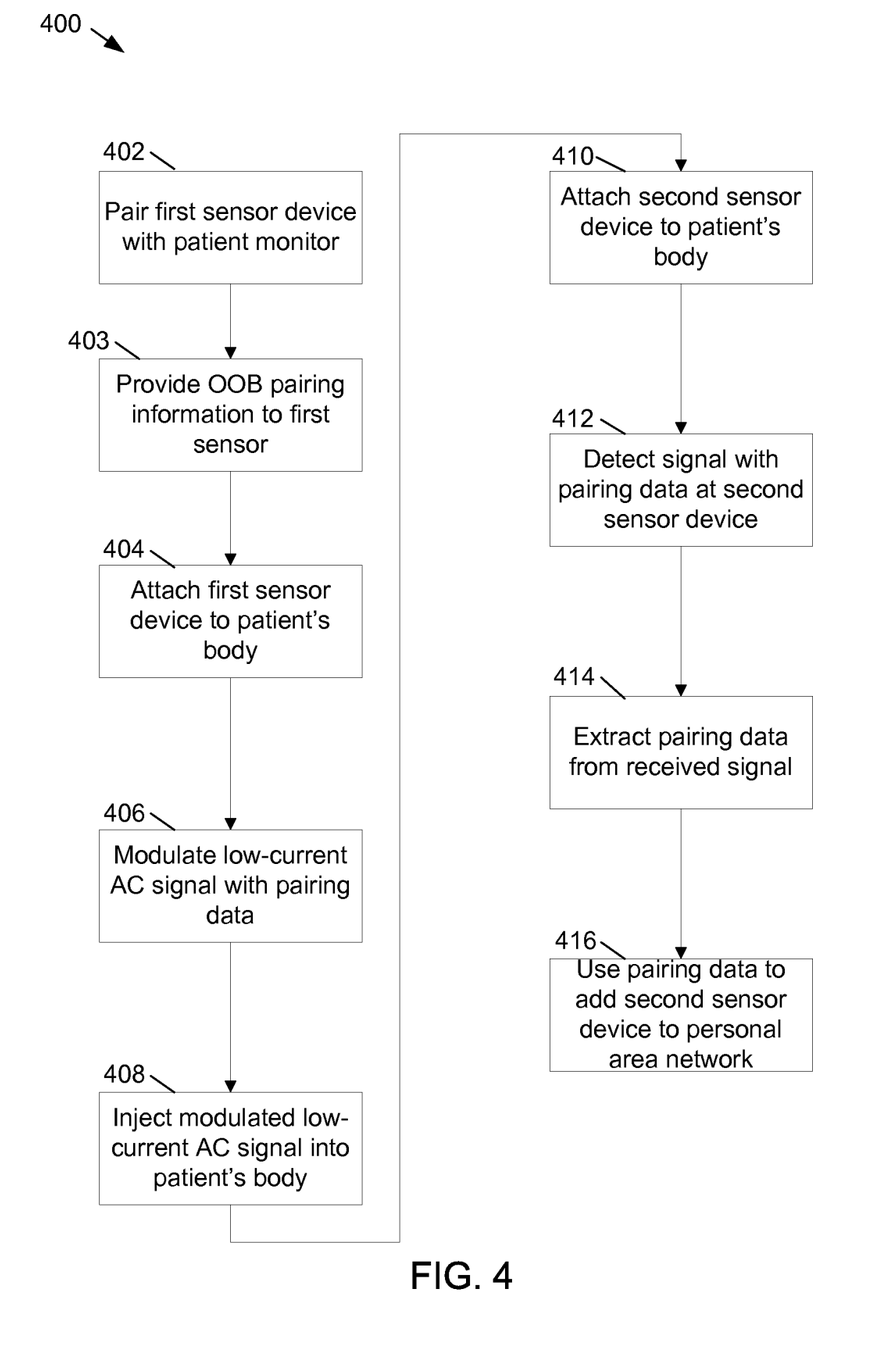
FIG. 4 shows a flowchart for a method of using out-of-band communications to pair a physiological sensor device attached to a patient's body to a patient monitor in a personal area network.

FIG. 4 shows a flowchart 400 for a method of using OOB communication to pair a physiological sensor device attached to a patient's body to a patient monitor, for example patient monitor 112, in a personal area network. At operation 402, a first sensor device is paired to a patient monitor. The first sensor device must be a sensor device capable of injecting a signal into the patient's body that can be modulated with data and detected by other sensors, such as modulating the low-current AC signal used in impedance pneumography as part of ECG. Other sensors such as an $SPO_2$ sensor or NIBP cuff may be modified to have a low-impedance connection to the body as well. The patient monitor 112 is a device capable of displaying sensor information. Typically, the patient monitor is mounted on a wall or roll-stand in the patient's room to provide convenient viewing for medical personnel.

The first sensor device and the patient monitor both incorporate Bluetooth technology, permitting the devices to be paired in a personal area network. The first sensor device and the patient monitor may be paired by manually entering pairing information into the patient monitor, by touching the first sensor device to the patient monitor or by another Bluetooth pairing method.

At operation 403, any OOB BT pairing information that the sensor does not already posses is provided to the sensor. If the OOB BT pairing information is limited to device discovery and/or OOB authentication and/or BT_Addr of the PAN gateway, then no additional OOB BT pairing information would be required. If the sensor is embedded or cabled to the gateway, then the OOB BT pairing information is already inherently available to the sensor. Similarly, if the gateway is on the body, perhaps disposed in a wristband with a connection to the body, then the BT pairing information is already available and steps 402 and 403 are not required.

At operation 404, the paired first sensor device is attached to the patient's body. At operation 406, a low-current AC signal, typically 100 to 200 microamperes peak to peak, is modulated with OOB BT pairing information. In the modulation process, the carrier is typically an AC signal with a frequency in the 40 to 60 kHz range. The pairing data is modulated onto the carrier and becomes the envelope of the modulated AC signal.

At operation 408, the first sensor device injects the low-current AC signal into the patient's body. The signal may be injected continually or it may be injected according to a predetermined duty cycle, for example once every second. The signal might only be injected upon an event, such as clinical input, patient motion or other event indicating a state change.

At operation 410, a second sensor device is attached to the patient's body. At operation 412, the second sensor device detects the low-current AC signal injected into the body by the first sensor device. At operation 414, the second sensor device demodulates the detected AC signal and extracts the OOB BT pairing information.

At operation 416, the extracted OOB BT pairing information is used to pair the second sensor device to the personal area network. Typically, the pairing is accomplished by sending a Bluetooth message with the pairing data from the second sensor device. The Bluetooth message is sent through the air so that it can be detected by the patient monitor. When the patient monitor determines that the pairing data in the message identifies the second sensor device as being on the patient, the patient monitor is paired to the second sensor device and the second sensor device is added to the personal area network.

Figure 5:
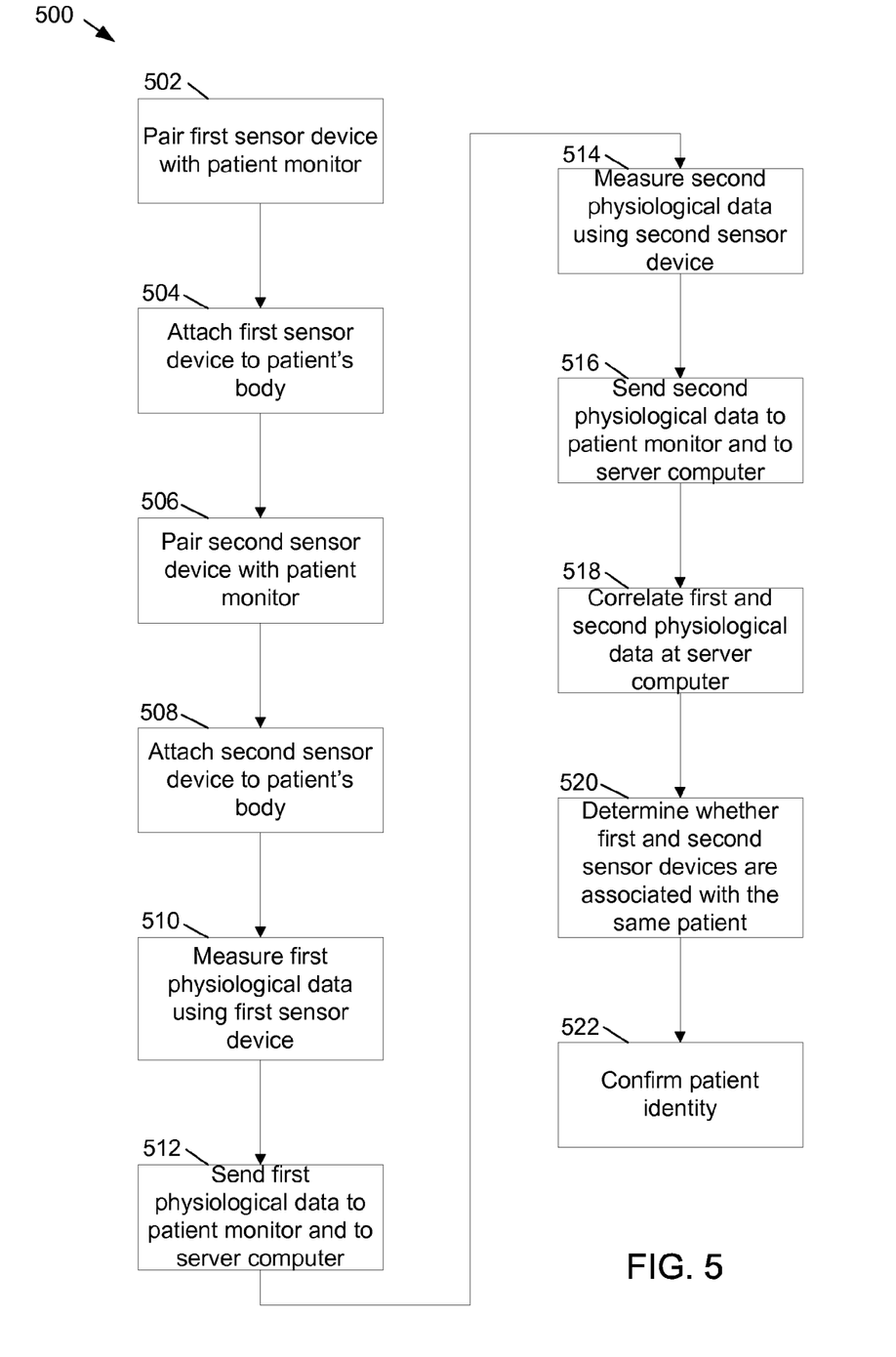
FIG. 5 shows a flowchart for a method of confirming a patient's identity using physiological data.

FIG. 5 shows a flowchart 500 for a method of confirming a patient's identity using physiological data. The physiological data is derived from sensor devices attached to a patient's body. The sensor devices used are those that measure data that can be correlated, such as heart rate and respiration rate. Typical physiological sensor devices that may be used include ECG sensors, $SPO_2$ sensors and blood pressure sensors.

Optionally, the patient identity may be entered into the patient monitor.

Then, at operation 502, a first sensor device is paired with a patient monitor, for example patient monitor 112, to form a personal area network. At operation 504, the first sensor device is attached to a patient's body. At operation 506, a second sensor device is paired with the patient monitor and joined to the personal area network. At operation 508, the second sensor device is attached to the patient's body.

At operation 510, the first sensor device measures first physiological data. For example, the first sensor device may be an ECG sensor that measures the heart rate of the patient. At operation 512, this data is sent to the patient monitor using Bluetooth. The data is also sent to server computer 118 via LAN/WAN connection 116. At operation 514, the second sensor device measures physiological data that can be correlated with the data from the first sensor. For example, the second sensor device may be an $SPO_2$ sensor that also measures heart rate. At operation 516, the second physiological data is sent to the patient monitor using Bluetooth. The data is also sent to server computer 118 via LAN/WAN connection 116.

At operation 518, the server computer or the patient monitor correlates the physiological data. For example, if the physiological data is the heart rate, the server computer determines the beat-to-beat intervals from each sensor. At operation 520, the server computer uses the correlation data to determine whether the physiological sensors are all on the same patient. If the data correlates and if the patient identity was optionally entered into the patient monitor, then at optional operation 522, the system begins to tag physiological data from the second sensor with the patient identity entered into the patient monitor.

Figure 6:
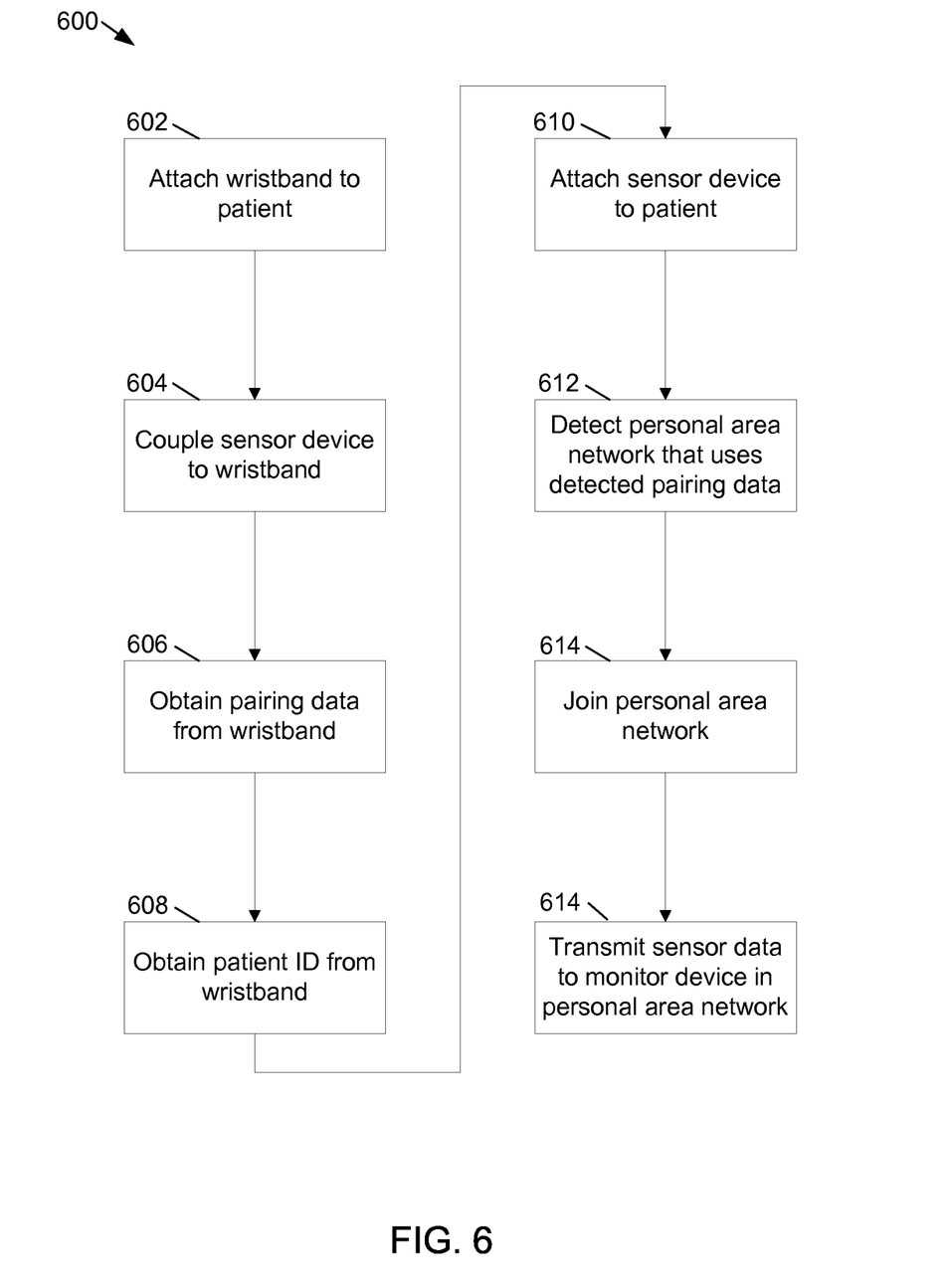
FIG. 6 shows a flowchart for a method for automatically identifying a patient in a medical setting using a wristband on the patient's body.

FIG. 6 shows a flowchart 600 for a method for automatically identifying a patient in a healthcare application using a wristband on the patient's body. At operation 602, the wristband, encoded with OOB BT pairing information and the PID, is attached to the patient. At operation 604, a sensor device is coupled to the wristband to extract, perhaps using RFID or other NFC mechanism to obtain encoded with OOB BT pairing information and the PID at operation 606 and the PID at optional operation 608. The pairing data may include a unique identifier for a personal area network that includes example patient monitor 112, such as the BT_Addr of the PAN gateway and may also contain authentication credentials.

At operation 610, the sensor device is attached to the patient. At operation 612, the sensor device detects a personal area network that uses the detected OOB BT pairing information. At operation 614, the sensor device joins the personal area network. At operation 614, the sensor transmits sensor data to a patient monitor in the personal area network. Typically, if the sensor device obtained the PID in step 608, then the PID and the physiological data are transmitted to the patient monitor.

A physiological sensor that incorporates Bluetooth technology is a computing device and typically includes at least one processing unit and system memory. Depending on the exact configuration and type of computing device, the system memory may be volatile (such as RAM), non-volatile (such as ROM, flash memory, etc.) or some combination of the two. System memory typically includes an embedded operating system suitable for controlling the operation of the sensor device. The system memory may also include one or more software applications, for example Bluetooth, and may include program data.

The various embodiments described above are provided by way of illustration only and should not be construed to limiting. Various modifications and changes that may be made to the embodiments described above without departing from the true spirit and scope of the disclosure.

What is claimed is:

1. A method for automatically adding a first sensor device to a first personal area network, the method comprising:
receiving a signal with out-of-band pairing data at the first sensor device, the first sensor device being disposed on a patient's body, the out-of-band pairing data having been injected into the patient's body by a second sensor device disposed on the patient's body and the out-of-band pairing data including a Bluetooth® address of the second sensor device;
extracting the pairing data from the received signal at the first sensor device;
transmitting a link key to the second sensor device to be used for authentication, wherein the link key is transmitted out-of-band and wherein the link key is generated based on both a Bluetooth® address of the first sensor device and the Bluetooth® address of the second device;
using the pairing data to add the first sensor device to the first personal area network, including sending the pairing data to a monitoring device using an in-band communication scheme;
determining, by the monitoring device, a correlation factor between the first sensor device and the second sensor device, wherein the correlation factor is calculated using one of the following physiological parameters detected by the first sensor device and the second sensor device: blood pressure, saturated oxygen content, heart rate, respiration rate or end-tidal carbon dioxide; and
using the correlation factor to determine if the first sensor device and the second sensor device are on the same patient.

2. The method of claim 1, wherein the out-of-band pairing data includes an identifier for the first personal area network.

3. The method of claim 2, wherein the identifier is a personal ID of the patient.

4. The method of claim 1, wherein the signal is a low-current AC signal that is modulated with the out-of-band pairing data.

5. The method of claim 4, wherein the low-current AC signal is between 50 to 300 microamperes peak to peak.

6. The method of claim 4, wherein extracting the pairing data from the received signal further comprises demodulating the received signal.

7. The method of claim 1, wherein the signal is received at the first sensor device via an antenna that is included in the first sensor device.

8. The method of claim 1, further comprising:
receiving a second link key from the second sensor device; and
authenticating by comparing the link key transmitted to the second sensor device and the second link key received from the second sensor device.

9. A method for automatically adding a first sensor device to a first personal area network, the method comprising:
receiving a signal with out-of-band pairing data at the first sensor device, the first sensor device being disposed on a patient's body, the out-of-band pairing data having been injected into the patient's body at periodic intervals by a second sensor device disposed on the patient's body;
extracting the pairing data from the received signal at the first sensor device; using the pairing data to add the first sensor device to the first personal area network;
determining, by a device, a correlation factor between the first and second sensor devices, wherein the correlation factor is calculated using one of the following physiological parameters detected by the first and second sensor device: blood pressure, saturated oxygen content, heart rate, respiration rate or end-tidal carbon dioxide; and
using the correlation factor to determine if the first and second sensor devices are on the same patient.

* * * * *

UNITED STATES PATENT AND TRADEMARK OFFICE
CERTIFICATE OF CORRECTION

| | | |
|---|---|---|
| PATENT NO. | : 9,000,914 B2 | Page 1 of 1 |
| APPLICATION NO. | : 12/723726 | |
| DATED | : April 7, 2015 | |
| INVENTOR(S) | : Baker et al. | |

It is certified that error appears in the above-identified patent and that said Letters Patent is hereby corrected as shown below:

On the title page item 75, State of residence for Kahlke: "WI" should read --OR--

Signed and Sealed this
Fifteenth Day of December, 2015

Michelle K. Lee
*Director of the United States Patent and Trademark Office*